(12) United States Patent
Kovac et al.

(10) Patent No.: US 8,636,643 B2
(45) Date of Patent: *Jan. 28, 2014

(54) METHOD FOR SUPPORTING VAGINAL CUFF

(75) Inventors: S. Robert Kovac, Atlanta, GA (US); James E. Cox, Corcoran, MN (US)

(73) Assignee: AMS Research Corporation, Minnetonka, MN (US)

( * ) Notice: Subject to any disclaimer, the term of this patent is extended or adjusted under 35 U.S.C. 154(b) by 86 days.

This patent is subject to a terminal disclaimer.

(21) Appl. No.: 13/023,652

(22) Filed: Feb. 9, 2011

(65) Prior Publication Data

US 2011/0137113 A1 Jun. 9, 2011

Related U.S. Application Data

(63) Continuation of application No. 11/243,802, filed on Oct. 5, 2005, now Pat. No. 7,901,346.

(60) Provisional application No. 60/666,457, filed on Mar. 28, 2005, provisional application No. 60/616,344, filed on Oct. 5, 2004.

(51) Int. Cl.
*A61F 2/00* (2006.01)

(52) U.S. Cl.
USPC .......................................................... 600/37

(58) Field of Classification Search
USPC .................. 600/29, 30, 37; 128/885; 606/151; 623/23.64–23.72
See application file for complete search history.

(56) References Cited

U.S. PATENT DOCUMENTS

| | | |
|---|---|---|
| 6,387,071 B1 | 5/2002 | Constantz |
| 6,592,515 B2 | 7/2003 | Thierfelder et al. |
| 6,911,003 B2 | 6/2005 | Anderson et al. |
| 6,929,599 B2 | 8/2005 | Westrum, Jr. |
| 7,131,944 B2 | 11/2006 | Jacquetin |
| 7,393,320 B2 | 7/2008 | Montpetit et al. |
| 7,407,480 B2 | 8/2008 | Staskin et al. |
| 7,494,495 B2 | 2/2009 | Delorme et al. |
| 7,901,346 B2 | 3/2011 | Kovac et al. |
| 2002/0103542 A1 | 8/2002 | Bilbo |
| 2003/0176762 A1 | 9/2003 | Kammerer |
| 2003/0220538 A1 | 11/2003 | Jacquetin |
| 2004/0006353 A1* | 1/2004 | Bosley et al. ................. 606/151 |
| 2004/0039453 A1 | 2/2004 | Anderson et al. |

(Continued)

FOREIGN PATENT DOCUMENTS

| | | |
|---|---|---|
| WO | WO02/38079 | 5/2002 |
| WO | WO03/073960 | 9/2003 |
| WO | WO03/096929 | 11/2003 |
| WO | WO2004/012626 | 2/2004 |

OTHER PUBLICATIONS

Staskin and Plzak, "Synthetic Slings: Pros and Cons," Female Urology, Current Urology Reports, vol. 3, pp. 414-417, 2002.

(Continued)

*Primary Examiner* — Christine Matthews
(74) *Attorney, Agent, or Firm* — Kagan Binder, PLLC

(57) ABSTRACT

Described are methods and devices useful for supporting posterior vaginal tissue for various purposes such as treating or preventing vaginal prolapse or enterocele, especially in a patient not having a uterus, the devices including implants designed to contact the vaginal cuff and connect to sacral anatomy such as the sacrum or the uterosacral ligaments.

6 Claims, 9 Drawing Sheets

(56) References Cited

U.S. PATENT DOCUMENTS

| | | |
|---|---|---|
| 2004/0106847 A1* | 6/2004 | Benderev .................. 600/37 |
| 2004/0116774 A1 | 6/2004 | Migliari |
| 2004/0249397 A1 | 12/2004 | Delorme et al. |
| 2004/0249473 A1 | 12/2004 | Delorme et al. |
| 2005/0080317 A1 | 4/2005 | Merade |
| 2005/0245787 A1 | 11/2005 | Cox et al. |
| 2005/0250977 A1 | 11/2005 | Montpetit et al. |
| 2005/0267325 A1 | 12/2005 | Bouchier et al. |
| 2006/0130848 A1 | 6/2006 | Carey |
| 2009/0012353 A1 | 1/2009 | Beyer |

OTHER PUBLICATIONS

"You know where you want to go . . . GPS for Pelvic Floor Repair," Gynecare Prolift Brochure, 2005.

* cited by examiner

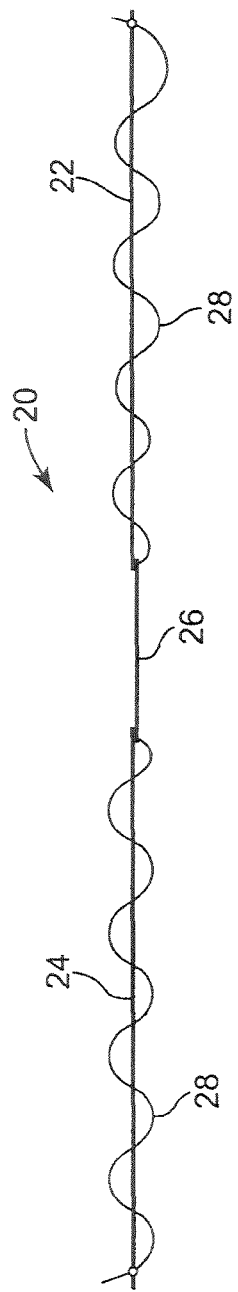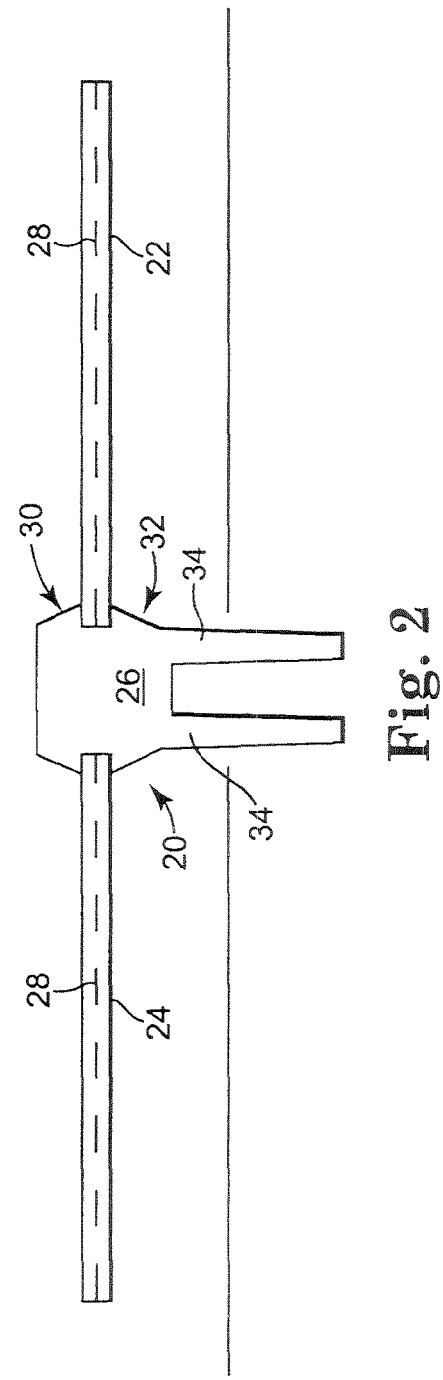

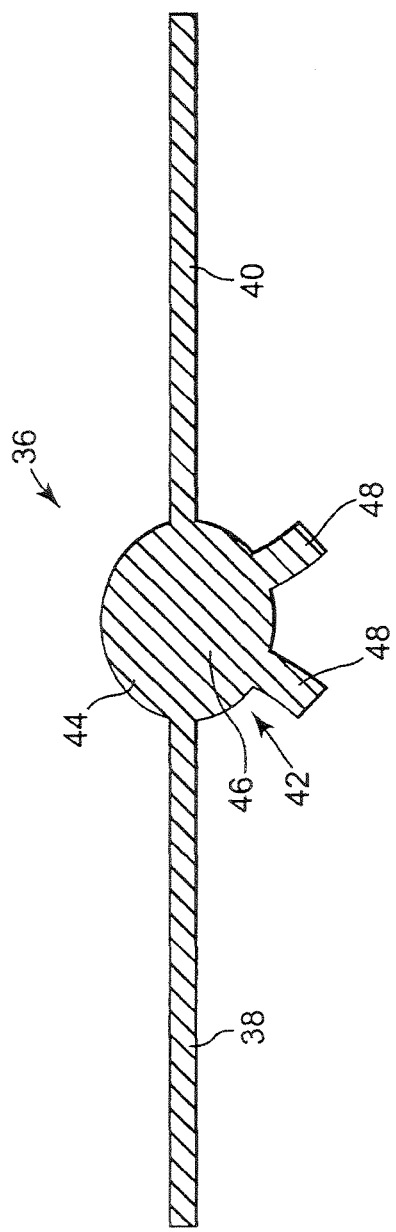

METHOD FOR SUPPORTING VAGINAL CUFF

PRIORITY CLAIM

The present non-provisional patent application is a continuation of U.S. Utility patent application Ser. No. 11/243,802 filed Oct. 5, 2005; which claims priority under 35 USC §119(e) from U.S. Provisional Patent Application having Ser. No. 60/616,344, filed on Oct. 5, 2004, and U.S. Provisional Patent Application having Ser. No. 60/666,457, filed on Mar. 28, 2005, wherein the entirety of said provisional patent applications are incorporated herein by reference.

FIELD OF THE INVENTION

The invention relates to methods and devices for preventing or treating vaginal prolapse, especially in women who have experienced a hysterectomy.

BACKGROUND

Female genital prolapse has long plagued women. With the increasing age of the U.S. population these problems will likely assume additional importance.

Vaginal prolapse develops when intra-abdominal pressure affects the position of the vagina, in severe cases causing the vagina to become positioned outside of the body. In a normal situation, the levator ani muscles close the pelvic floor and support the vagina. This results in little force being applied to the fascia and ligaments that support the vagina. Increases in abdominal pressure, failure of the muscles to keep the pelvic floor closed, and damage to ligaments and fascia, can all contribute to the development of prolapse.

Conditions of posterior vaginal wall prolapse can involve descent of the rectum into the vagina, often termed a rectocele, or the presence of small intestine in a hernia sac between the rectum and vagina, called an enterocele. Broadly, there are four types based on suspected etiology. Congenital enteroceles are thought to occur because of failure of fusion or reopening of the fused peritoneal leaves down to the perineal body. Posthysterectomy vault prolapse can result from a lack of support from detachment of the uterosacral ligaments from the uterus at the time of hysterectomy. Enterocele may occur because of failure to reapproximate the superior aspects of the pubocervical fascia and the rectovaginal fascia at the time of surgery. Iatrogenic prolapse may occur after a surgical procedure that changes the vaginal axis, such as certain surgical procedures for treatment of incontinence. With regard to rectoceles, the most common type of rectocele results from disruption of connective tissue supports of the rectovaginal fascia from its normal attachments to the uterosacral ligaments. Posterior or posthysterectomy enteroceles may accompany rectoceles.

Several factors have been implicated as being involved in causing vaginal prolapse. It is thought that individual women have differing inherent strength of the relevant connective tissue. Further, loss of connective tissue strength might be associated with damage at childbirth, deterioration with age, poor collagen repair mechanisms, and poor nutrition. Loss of muscle strength might be associated with neuromuscular damage during childbirth, neural damage from chronic straining, and metabolic diseases that affect muscle function. Other factors involved in prolapse include increased loads on the supportive system as seen in prolonged lifting or chronic coughing from chronic pulmonary disease, or some disturbance in the balance of the structural support of the genital organs. Obesity, constipation, and a history of hysterectomy have also been implicated as possible factors. In specific, the vaginal angle may be altered upon removal of the uterus, causing increased pressure at a more acute angle, accelerating the prolapse.

Vaginal prolapse conditions can lead to discomfort, urinary incontinence, and incomplete emptying of the bladder. Posterior vaginal prolapse may additionally cause defecatory problems such as tenesmus and difficulty in stool evacuation.

Various techniques have been used to attempt to correct or ameliorate prolapse and prolapse symptoms, with varying degrees of success. Nonsurgical treatment of prolapse involves measures to improve the factors associated with prolapse, including treating chronic cough, obesity, and constipation. Other nonsurgical treatments may include pelvic muscle exercises or supplementation with estrogen. These therapies "may" alleviate some symptoms and temporarily provide some relief to the patient, but the actual hernia will remain. Vaginal pessaries are the primary type of nonsurgical treatment, but potential complications can occur such as vaginal wall ulceration.

Surgical treatments of posterior prolapse can involve vaginal and abdominal procedures to reapproximate the attenuated tissue using sutures or a biological or synthetic implant to provide continuing support of the reapproximated tissue following the procedure. Implants that have been used to address pelvic organ prolapse are described, e.g., in U.S. Patent Publication No. 2004/0039453 (Ser. No. 10/423,662), and U.S. patent application Ser. No. 10/834,943, entitled "Method and Apparatus for Treating Pelvic Organ Prolapse," filed Apr. 30, 2004, these patent applications being incorporated entirely herein by reference.

An example of a specific implant product designed for treating conditions of vaginal vault prolapse include the APOGEE® product from American Medical Systems. Very generally, these devices are designed to be implanted in a manner to support vaginal tissue. The APOGEE devices and similar products can include various designs, such as "strips" of a single material or pieces of the same or different materials connected together (e.g., mesh, tape, optionally including synthetic or biological tissue portions) to form an implant that can be attached at one portion to vaginal tissue, with another portion attached at a position of the anatomy that supports the vaginal tissue.

SUMMARY

The invention relates to devices, methods, and kits, useful for supporting vaginal tissue in a patient who does not have a uterus. The invention relates to an implant that is designed specifically to support the vaginal cuff remaining after removal of the uterus and cervix, e.g., to support the pericervical ring created upon removal of the uterus and cervix. The support attaches to posterior vaginal tissue remaining after removal of the uterus and cervix, and attaches also to anatomy to support the vaginal tissue, at or around the sacrum such as to uterosacral ligaments or to the sacrum itself (i.e., to a component of the sacral anatomy). The implant can be attached to a component of the sacral anatomy by any chemical or mechanical attachment such as by an adhesive, a suture, a bone screw or bone anchor, a staple, or any other fastener for tissue or bone.

According to embodiments of the invention, a surgeon uses an implantable device ("implant") such as a support member, a support strip, or an implant that includes a support portion attached to two extension portions, to attach to the pericervical ring or vaginal cuff remaining following removal of the uterus and cervix. The implant can be attached to uterosacral ligaments or the sacrum to support the implant and the vaginal vault. The implant may optionally be further supported by attachment of extension portions of the implant to other anatomical features, e.g., a tissue path to an external incision, to thereby further support the vaginal vault.

An implant can include a support portion for attachment to the vaginal cuff. Specific examples of implants can include a support portion designed to be attached to the vaginal cuff, e.g., to fit around and contact different portions of the vaginal cuff including the apex. The support portion can also include one or more features or areas to attach to a component of the sacral anatomy such as the uterosacral ligaments or the sacrum, to support the vagina and treat or prevent vaginal wall prolapse. The support portion can be designed and installed to prevent possible future enterocele formation.

Optionally the implant can include one or two extension portions attached to the support portion and extending in opposite directions from the support portion. Exemplary implants can include two extension portions extending in opposite directions from a central support portion. The extension potions can be sized and shaped to extend from the central support portion, to be attached to an anatomical position that provides support for the central support portion attached to the vaginal cuff. For example, extension portions can be led through tissue paths from the interior pelvic area to external incisions, with the extension portions becoming ingrown in a manner to support the central support portion of the implant attached to the vaginal cuff.

The implant can be installed in a patient who does not have a uterus, e.g., after removal of the uterus and cervix. The implant can be installed at the time of removal of the uterus as part of a hysterectomy procedure. Alternately, the implant can be installed later, in a subsequent surgical procedure, in a patient who has had an earlier hysterectomy, such as during a subsequent procedure to treat or prevent vaginal vault prolapse and enterocele formation.

An exemplary method according to the invention can involve, generally, introduction of an implant into the pelvic region (e.g., transvaginally or abdominally) and attaching the implant to the vaginal cuff. The implant is also attached to a component of sacral anatomy such as the uterosacral ligaments or directly to the sacrum itself, to support the vaginal vault. In a patient who has sufficiently intact uterosacral ligaments, a surgeon may opt to keep these ligaments in place and attach the implant to the uterosacral ligaments. In instances where the uterosacral ligaments are damaged or not completely intact, not of sufficient length, or for another reason, the surgeon may opt to attach the implant directly to the sacrum.

Extension portions of an implant can be attached anatomically to support the support portion of an implant attached to the vaginal cuff. An exemplary mode of placement of extension portions of an implant can be bilateral passage of the extension portions through tissue paths leading to an external incision, such as an external incision at a perirectal region as discussed in copending U.S. patent application Ser. No. 10/834,943, filed Apr. 30, 2004, entitled "Method and Apparatus for Treating Pelvic Organ Prolapse. This exemplary method can include steps of establishing a first pathway between the external perirectal region of the patient and the region of the ischial spine space in tissue generally on one side of the vaginal cuff, and establishing a second corresponding pathway in tissue on the contralateral side of the vaginal cuff. Exemplary implants as described, including a central support portion and two extension portions, can be attached to the vaginal cuff in such a way as to allow repositioning of the vaginal cuff to an anatomically appropriate location. The extension portions of the implant can then be introduced through the respective bilateral tissue pathways. The extension portions can be adjusted so that the implant and central support portion are located in a therapeutic relationship to the vaginal cuff being supported.

An aspect of the invention relates to a method of supporting vaginal tissue. The method includes: providing a surgical implant comprising a support portion, attaching the support portion to vaginal or cervical tissue remaining upon removal of a uterus, cervix, or both, and attaching the support portion to a component of sacral anatomy.

Another aspect of the invention relates to a transvaginal method of supporting vaginal tissue. The method includes: providing a surgical implant, transvaginally attaching the surgical implant to vaginal or cervical tissue remaining after removal of a uterus, cervix, or both, and transvaginally attaching the support portion to a component of sacral anatomy.

Another aspect of the invention relates to a surgical implant. The implant includes a central support portion and two extension portions extending longitudinally from the central support portion. The central support portion includes: an anterior lobe extending laterally from the extension portions and a posterior lobe extending laterally from the extension portions in a direction opposite of the anterior component. The posterior lobe includes two lobe extensions.

BRIEF DESCRIPTION OF THE DRAWINGS

FIGS. 2 and 2A illustrates an example of a surgical implant as described herein, with FIG. 2A showing side view and FIG. 2 showing a top view.

FIG. 3 illustrates an example of a surgical implant as described herein.

Figure 1:
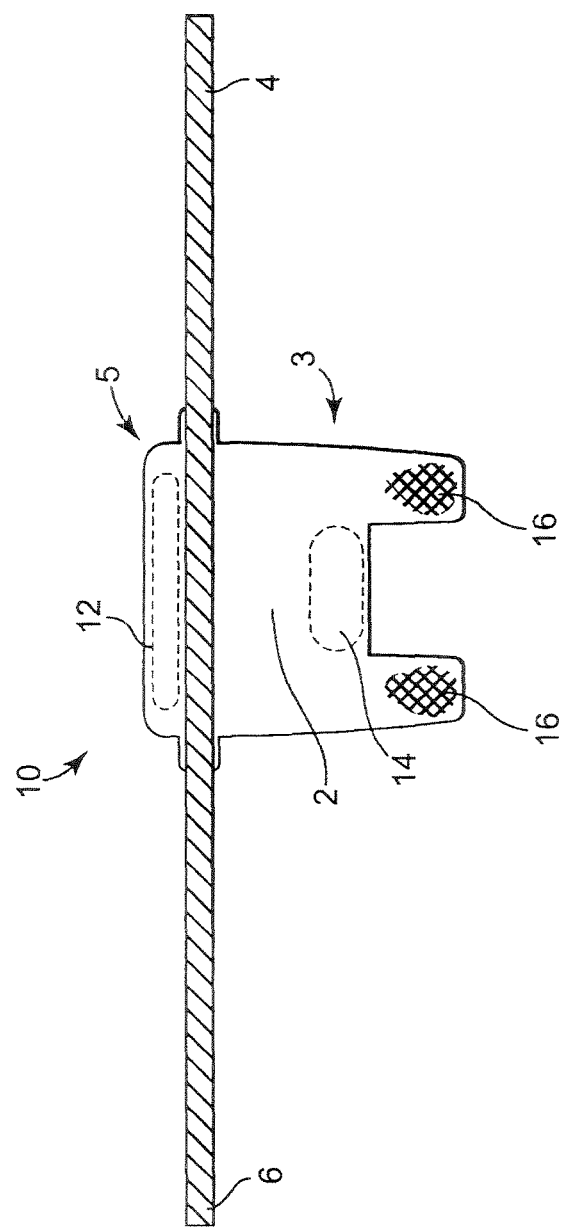
FIG. 1 illustrates an example of a surgical implant as described herein.

All figures are exemplary, schematic, and are not necessarily to scale.

DETAILED DESCRIPTION

The invention relates to devices, methods, and kits, useful for supporting vaginal tissue in a patient who does not have a uterus. The invention relates to an implant that is designed specifically to support vaginal cuff and optionally cervical tissue remaining after removal of the uterus, the cervix, or both, e.g., to support the pericervical ring created upon removal of the uterus, cervix, or both. The support attaches to vaginal or cervical tissue remaining after removal of the uterus and optionally cervix, and attaches also to anatomy to support the vaginal tissue, at or around the sacrum such as uterosacral ligaments or the sacrum itself (i.e., a component of the sacral anatomy). The implant can be attached to a component of the sacral anatomy by any chemical or mechanical attachment such as by an adhesive, a suture, a bone screw or bone anchor, a staple, or any other fastener for tissue or bone.

A useful implant can be any implant that can be fit to the vaginal cuff following removal of the uterus, cervix, or both, optionally with suturing of vaginal tissue to close the vaginal vault. (The term "vaginal cuff" is used herein to refer to the vaginal cuff, and also the vaginal cuff as that tissue may also include the cervix or a portion of the cervix if cervical tissue remains following a hysterectomy.") The implant can also attach to a component of the sacral anatomy such as a uterosacral ligament or the sacrum to support the vaginal cuff in a desired position.

Exemplary implants can consist of or include a support portion sized and shaped to attach to a vaginal cuff location where the uterus and optionally the cervix has been removed, in a patient who has had a hysterectomy. The vaginal cuff may be sutured to close the vaginal vault and the implant may fit over the vaginal cuff. The support portion can be used to close or cover the vaginal cuff by contacting different portions of vaginal cuff tissue. For example, the support portion can be sized and shaped to contact a posterior portion of the vaginal cuff (e.g., rectovaginal fascia) and also an anterior portion of the vaginal cuff (e.g., pubovaginal fascia), to cover the vaginal cuff from the posterior to the anterior locations of the vaginal cuff, including the apex.

Exemplary implants can include a central support portion and two extension portions, the central support portion being useful to attach to the vaginal cuff and a component of the sacral anatomy. The central support portion can be sized and shaped to attach to the vaginal cuff at multiple locations such as at a posterior location (e.g., rectovaginal fascia) and an anterior location (e.g., pubovaginal fascia). The central support portion can also be adapted (e.g., sized and shaped) to attach to a component of sacral anatomy such as the uterosacral ligaments or sacrum. As an example, a posterior lobe of a central support portion can include one or more lobe extensions that are of a size and shape to be attached to the sacrum or to one or more uterosacral ligaments.

Extension portions connected to and extending from a central support portion can be useful to attach to other anatomical features to provide further support for the central support portion and the attached vaginal cuff. The two extension portions can extend from the central support portion as elongate "arms" or extensions that are attached to other anatomy, such as by extending through a tissue path to an external incision. See, e.g., U.S. patent publication number 2005/0080317, having U.S. Ser. No. 10/684,861, filed Oct. 14, 2003, the entirety of which is incorporated herein by reference.

The total shape of exemplary implants, e.g., including a central support portion and extension portions, can accommodate surgical placement of the implant to attach to anatomy as described herein to support the vaginal cuff. For an implant that includes a central support portion and two extension portions, the extension portions can be connected at opposing sides of the central support portion and can extend longitudinally in opposite directions away from the central support portion. For these exemplary implants the central support portion is located between the two extension portions to bridge the two extension portions together, and the central support portion is wider than the two extension portions in that the central support portion extends laterally beyond the width of the extension portions. These portions or "lobes" of the central support portion that extend laterally beyond the width of the extension portions can be referred to as anterior and posterior lobes of the central support portion. Thus, a central support portion can be referred to as comprising an anterior lobe extending laterally from the extension portions and a posterior lobe extending laterally from the extension portions in a direction opposite of the anterior component.

A support portion can be shaped to fit vaginal and optionally cervical tissue remaining after a hysterectomy (i.e., sometimes referred to as the "vaginal cuff," for purposes of this description) and may be generally rectangular, round, oval, oblong, etc., with the anterior lobe and the posterior lobe being of the same or different size or shape relative to each other. According to particular embodiments, a posterior lobe of a support portion can include two lobe extensions that are each adapted to attach to the sacrum or to a uterosacral ligament. In particular embodiments, an implant can be prepared and supplied with lobe extensions that are sufficiently long to reach the sacrum—should that implant be used in a procedure that includes attaching the lobes to the uterosacral ligaments, the lobes can be trimmed in length to accommodate the reduced distance from the installed support portion to uterosacral ligaments.

Lobe extensions can be rectangular or square extensions off of a main lobe body, optionally including a curvature if desired, and extending a distance from the main lobe body sufficient to extend from the sacrum to the vaginal vault or cuff following hysterectomy with removal of the cervix, such as a distance in the range from 1 to 5 centimeters. The lobe extensions can be trimmed for accommodating distances at the low end of this range. The width of a lobe extension can be sufficient to allow attachment to a uterosacral ligament or the sacrum, such as a width in the range from about 0.5 centimeters to 1.5 centimeters.

Materials useful for an implant (e.g., support portion, extension portion, central support portion, etc.) can be any of a variety of synthetic or biologic materials. Exemplary extension and support portions can be prepared from any combination of synthetic and biologic or natural materials. For example, an extension portion or a support portion may be made of a synthetic mesh; e.g., an entire implant consisting of a support portion alone or a central support portion and extension portions may be made entirely of a one-piece mesh. In other embodiments exemplary extension portions can be of synthetic mesh and a central support portion can be of a synthetic or biologic tissue material. Components of a multi-piece or multi-material implant may be pre-attached or pre-assembled, e.g., attached during manufacture, so a surgeon is not required to spend significant time cutting, connecting, or otherwise assembling the pieces of an implant prior to a surgical installation procedure.

A synthetic implant material can be any synthetic material that can be useful in an implantable surgical device, such as a biocompatible polymeric material or a biocompatible non-polymeric synthetic material. Examples of useful polymeric materials that may be useful in a polymeric mesh include thermoplastic polymeric materials such as polyolefins (e.g., polypropylenes), polyurethanes, acetel materials, Teflon® materials, and the like; thermoset materials such as silicones; and materials that are otherwise curable, e.g., that can be cured by ultraviolet radiation or chemical reactions, including curable materials such as curable urethanes, epoxies, acrylates, cyanoacrylates, and the like. Any of these materials may be homopolymers, copolymers, or a blend or other combination of homopolymers, copolymers, or both. Other suitable synthetic materials include metals (e.g. silver filigree, tantalum gauze mesh, and stainless steel mesh).

A synthetic implant material may be in any form, such as a continuous, solid, or semi-continuous (e.g., perforated) film; or in the form of combined fibers or strands, e.g., a braided, knit, tied, mesh, woven, non-woven, or fabric-type of material; or combinations of these. Certain embodiments of implants include a synthetic implant portion in the form of a polymeric mesh material. The mesh material includes one or more woven, knitted or inter-linked polymeric filaments or fibers that form multiple fiber junctions throughout the mesh. The fiber junctions may be formed via weaving, knitting, braiding, joining, ultrasonic welding or other junction forming techniques, including combinations thereof, leaving openings or pores ("interstices") between elements of the fibers. The size of the interstices mesh may be sufficient to allow tissue in-growth and fixation within surrounding tissue.

Many different types of synthetic film and mesh materials are known and may be suitable for use as a portion or piece of an implant such as an extension portion or a central support portion. These materials may be prepared from biocompatible materials that may be bioabsorbable or non-bioabsorbable, e.g., in the form of mesh materials. Suitable materials include cotton, linen, silk, polyamides (polyhexamethylene adipamide (nylon 66), polyhexamethylene sebacamide (nylon 610), polycapramide (nylon 6), polydodecanamide (nylon 12), and polyhexamethylene isophthalamide (nylon 61), and copolymers and blends thereof), polyesters (e.g., polyethylene terephthalate, polybutyl terephthalate, copolymers and blends thereof), fluoropolymers (e.g., polytetrafluoroethylene and polyvinylidene fluoride), polyolefins (e.g., polypropylene, including isotactic and syndiotactic polypropylene and blends thereof, as well as blends composed predominantly of isotactic or syndiotactic polypropylene blended with heterotactic polypropylene, and polyethylene), silicone, polygalactin, Silastic, polycaprolactone, polyglycolic acid, poly-L-lactic acid, poly-D-L-lactic acid and polyphosphate esters.

Commercial examples of polymeric materials for use in an implant include MARLEX (polypropylene) available from Bard of Covington, R.I.; PROLENE (polypropylene) and PROLENE Soft Polypropylene Mesh or Gynemesh (nonabsorbable synthetic surgical mesh), both available from Ethicon, of New Jersey; MERSILENE (polyethylene terephthalate) hernia mesh also available from Ethicon; GORE-TEX (expanded polytetrafluoroethylene) available from W. L. Gore and Associates, Phoenix, Ariz.; INTEPRO™ polypropylene materials, and the polypropylene material used in the commercially available SPARC® sling system, each available from American Medical Systems, Inc. of Minnetonka, Minn. Commercial examples of absorbable materials include DEXON (polyglycolic acid) available from Davis and Geck of Danbury, Conn., and VICRYL available from Ethicon.

Suitable non-synthetic (biologic) implant materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium, and fascia lata.

According to certain embodiments of implants, various additional components and features can be incorporated for added utility or convenience, such as components and features that facilitate installation of a device during a surgical procedure. For instance, a tensioning member (e.g., suture) may be attached to an implant along a portion or entire length of an extension member for use in adding tension or in positioning an implant or a portion (e.g., extension) of an implant. Alternately or in addition, an exemplary implant may include a removable sheath such as a plastic, transparent elongate tube, etc., that can cover a portion or entire length of an extension portion of an implant to facilitate installation by allowing a surgeon to apply tension or pressure on the sheath to indirectly apply pressure or tension to the extension portion. Additionally or alternately, extension portions of an implant may include a connector or "dilator" tip at an end of an extension member distal from a central support member, the connector being able to cooperate with an insertion tool (e.g., needle, tunneler, etc.) during a surgical procedure to either push or pull the connector using the end of the insertion tool. For example, a tip may be a rigid plastic tip or "dilator" constructed to attach to an end of an elongate insertion tool by snapping or otherwise securing to the end of the tool. The tool can then be used to push or pull the connector through a tissue passage to also bring the extension portion of the implant through the tissue passage.

Different components of exemplary implants, e.g., support portion, central support portion, extension portions, tensioning members (e.g., sutures), etc., can be formed separately and assembled by methods such as those described in pending patent application having U.S. Ser. No. 11/115,655, filed on Apr. 26, 2005, entitled "SURGICAL IMPLANTS AND RELATED METHODS," the entirety of which is incorporated herein by reference.

FIG. 1 illustrates a specific example of an implant. FIG. 1 shows support member or "implant" 10 having central support portion 2 and two extension portions or end strips ("extension portions"), 4 and 6. Central support portion 2 includes posterior lobe 3 extending in one direction laterally from longitudinally-extending extension portions 4 and 6, and anterior lobe 5 extending in the other lateral direction from longitudinally-extending extension portions 4 and 6. According to this embodiment, a surgeon can attach posterior lobe 3 of central portion 2 to the posterior rectovaginal facia (septum) (RVF), such as at the area designated by outlined area 14 of posterior lobe 3. Anterior lobe 5 (e.g., at outlined portion 12) can be attached to the pubovaginal cervical fascia (PVCF). One or more points or sections of central support portion 2, such as lobe extensions 16, can then be attached bilaterally to the uterosacral ligaments (USL).

FIGS. 2 and 2A also illustrates an implant (FIG. 2A in cross section). As illustrated, implant 20 may be prepared from polymeric (e.g., polypropylene) mesh strip extension portions 22 and 24 attached (e.g., sutured) to central support portion 26, which may be synthetic or biologic. Sutures 28 extend from central support portion 26 along the lengths of each extension portion 22 and 24. Sutures 28 can function as tension control members and as repositioning means to effect positioning, tightening, or loosening, of the extension portions or the implant.

When implant 20 is installed, anterior lobe 30 can be attached to pubovaginal cervical fascia (PVCF) and posterior lobe 32 can be attached to rectovaginal facia (RVF). Lobe extensions 34 are sufficiently long to be attached to the sacrum. Alternately, lobe extensions 34 can be trimmed to a length to accommodate attaching each lobe extension to a uterosacral ligament (USL). Far ends of each of extension portions 22 and 24 can then be attached anatomically to support the posterior vaginal wall, e.g., using external incisions at the perirectal region to extend extensions 22 and 24 through pathways in tissue at the regions of the ischial spine, with each of extensions 22 and 24 extending from each side of the cervical ring.

FIG. 3 illustrates another example of an implant. FIG. 3 shows implant 36 having central support portion 42 and extension portions 38 and 40. As illustrated all of implant 36 is formed from a single piece of mesh by cutting to the shape of central support portion 42 and extension portions 38 and 40. Central support portion 42 includes anterior lobe 44 extending in one direction laterally from longitudinally-extending extension portions 38 and 40, and posterior lobe 46 extending in the other lateral direction from longitudinally-extending extension portions 38 and 40. Posterior lobe 46 also includes lobe extensions 48. When installed, posterior lobe 46 can be attached to the posterior rectovaginal facia (septum) (RVF) and anterior lobe 44 can be attached to the pubovaginal cervical fascia (PVCF). Lobe extensions 48 can be attached bilaterally to the uterosacral ligaments (USL), or may be attached to the sacrum.

Figure 4:
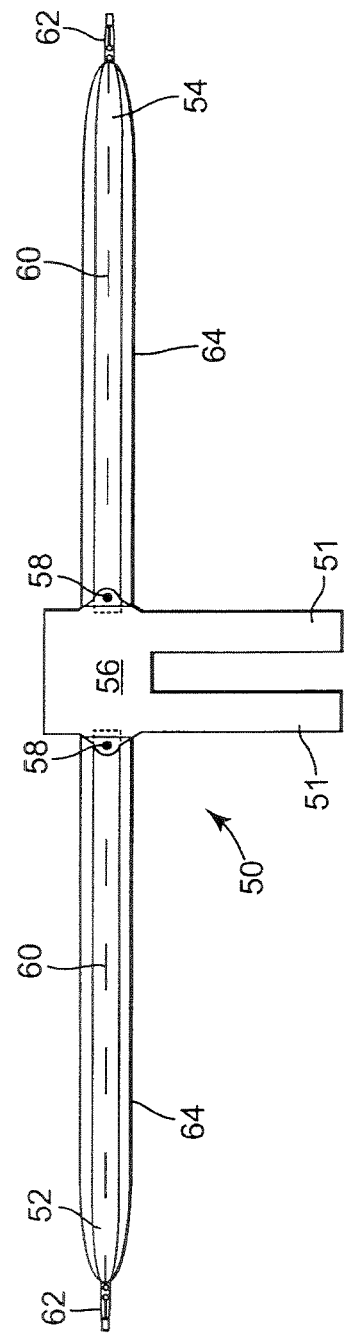
FIG. 4 illustrates an example of a surgical implant as described herein.

Another exemplary pelvic implant is at FIG. 4, showing implant 50 that can be useful as a pelvic implant. Central support portion 56 can be attached to vaginal tissue and lobe extensions 51 are sufficiently long to be attached to the sacrum or may be trimmed to a length to accommodate attaching each lobe extension 51 to a uterosacral ligament (USL). Implant 50 includes extension portions 52 and 54 connected to central support portion 56. Sutures 60, which are optional and not required, extend along the lengths of each of extension 52 and 54. In the illustration, polymeric rivets 58 secure extension portions 52 and 54 to central support portion 56 and to sutures 60. Optional tips (or "dilators"), or other connection mechanisms, 62 are attached at each of the non-attached ends of extension portions 52 and 54. Tips 62 can be, e.g., rigid plastic dilator tips that are shaped to connect to an end of an implantation device or tool such as a needle. Also shown are optional sheaths or covers 64, which can be flexible, e.g., transparent covers that extend over the lengths of each of extensions 52 and 54 from rivet 58 to dilator 62, which is crimped over covers 64. Covers 64 can be useful, e.g., as protection for extensions 52 and 54, and also for installation of implant 50, by being sufficiently stiff and non-elastomeric to allow the extensions to be pulled through a tissue path by pulling on cover 64.

According to exemplary methods of the invention, a surgeon can attach a support portion of an implant to the vaginal cuff. A surgeon can attach the posterior rectovaginal fascia (septum) to the support portion, and then attach the pubovesicle cervical fascia to another portion of the support portion. The support portion (e.g., points or pieces along the bottom of the central support portion) can also be attached or connected to the sacrum or bilaterally to the uterosacral ligaments. This may essentially rebuild the cervical ring and support the cervical ring by attachment to the sacrum or uterosacral ligaments. Extension portions of an implant, attached to the support portion, may be used to further support the vaginal tissue, e.g., by extending bilaterally to supporting anatomy.

Figure 5:
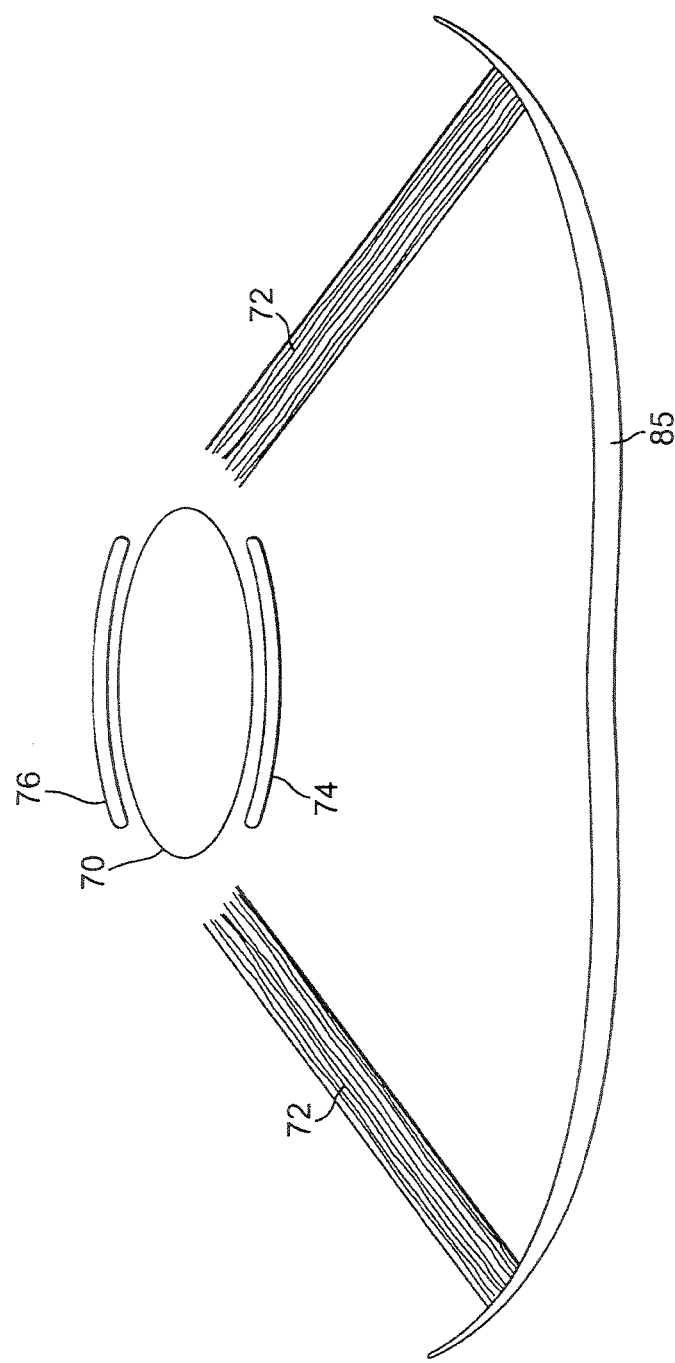
FIG. 5 illustrates relevant pelvic anatomy related to methods as described herein, prior to installation of an implant.

Exemplary procedures can be useful in female patients having had a hysterectomy with removal of the cervix. FIG. 5 illustrates an example of relevant pelvic anatomy following a hysterectomy, where the cervix has been removed. As shown, vaginal cuff 70 remains, as do uterosacral ligaments 72, which have been detached from the pericervical ring during the hysterectomy. Pubocervical fascia 76 is located at the anterior of vaginal cuff 70, and rectovaginal fascia 74 is located at the posterior of vaginal cuff 70. Sacrum 85 is also shown.

Figure 6:
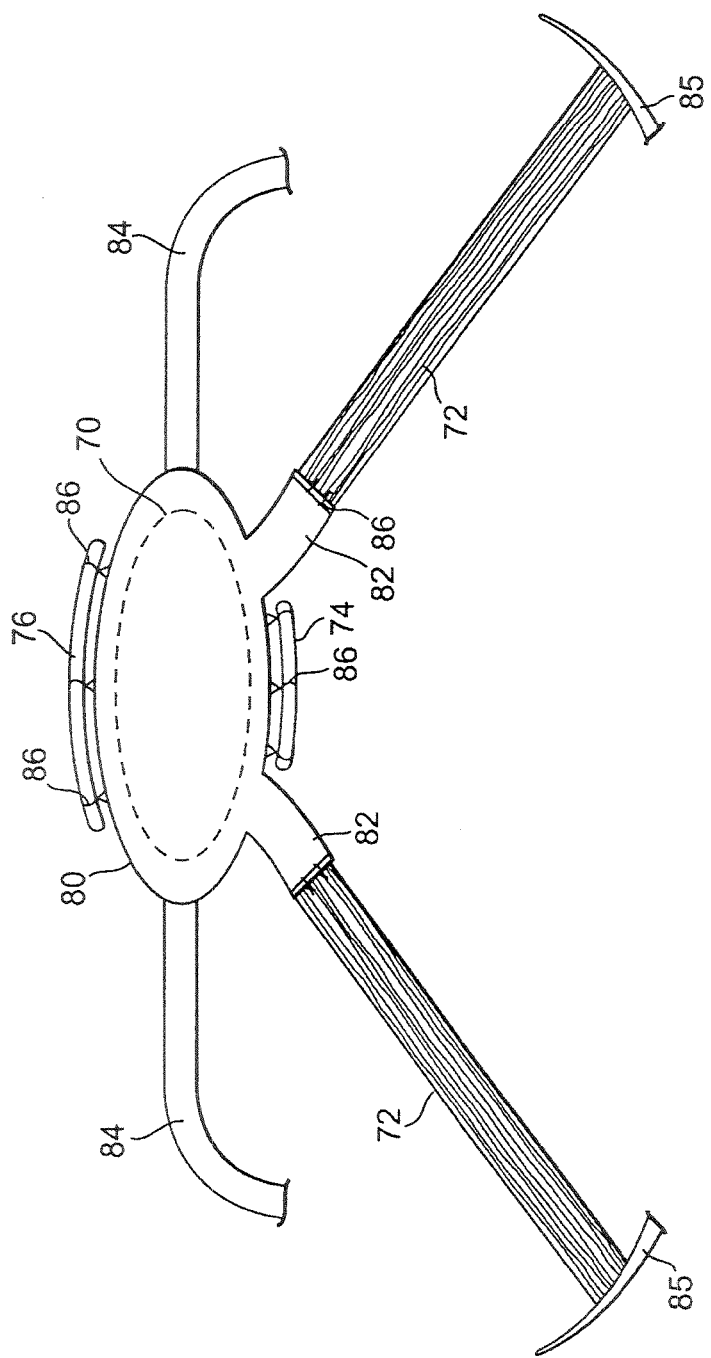
FIG. 6 illustrates relevant pelvic anatomy related to methods as described herein, including an implant.

Referring now to FIG. 6, vaginal cuff 70 is illustrated in dashed lines, beneath central support portion 80. Central support portion 80 includes two lobe extensions 82. Two extension portions 84, which may be mesh strips, tape, or the like, extend bilaterally from central support portion 80. Central support portion 80 is attached anteriorly to pubocervical fascia 76 and posteriorly to rectovaginal fascia 74, over the pericervical ring (at the vaginal cuff) opened as a result of the removal of the cervix with the hysterectomy. Sutures 86 are used to attach tissue to central support portion 80 and extensions 82. Uterosacral ligaments 72, detached from the pericervical ring with the hysterectomy, can be attached to lobe extensions 82 to support central support portion 80 and the pericervical ring and vaginal cuff 70. Accordingly, lobe extensions 82 are of a length to attach to uterosacral ligaments 72. Extension portions 84 extend through a tissue passage to be placed at or approximately at the level of the pericervical ring.

Figure 7:
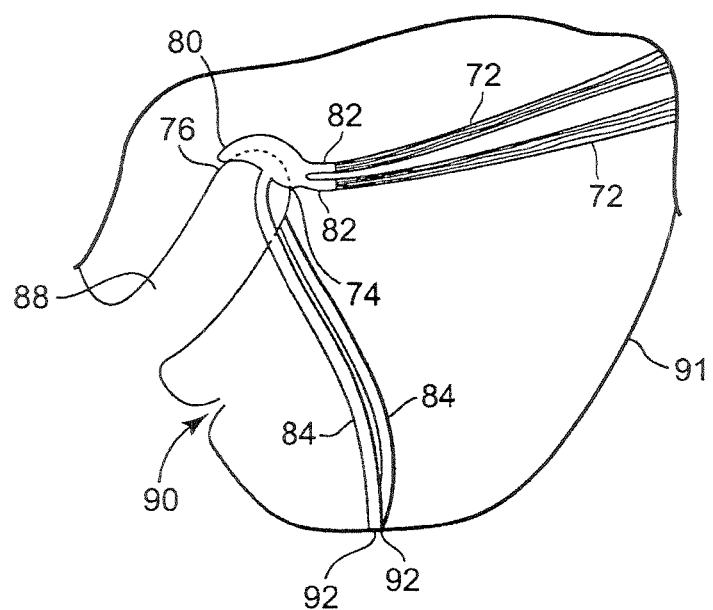
FIG. 7 illustrates relevant pelvic anatomy related to methods as described herein, including an implant.

FIG. 7 illustrates the anatomy following installation of an implant, from a side three-dimensional view, relative to vagina 88, buttock 91, and rectum 90. As seen in FIG. 7, extension portions 84 extend from central support portion 80 through tissue paths to external incisions 92. In this exemplary embodiment, lobe extensions 82 attach to uterosacral ligaments 72.

Figure 8:
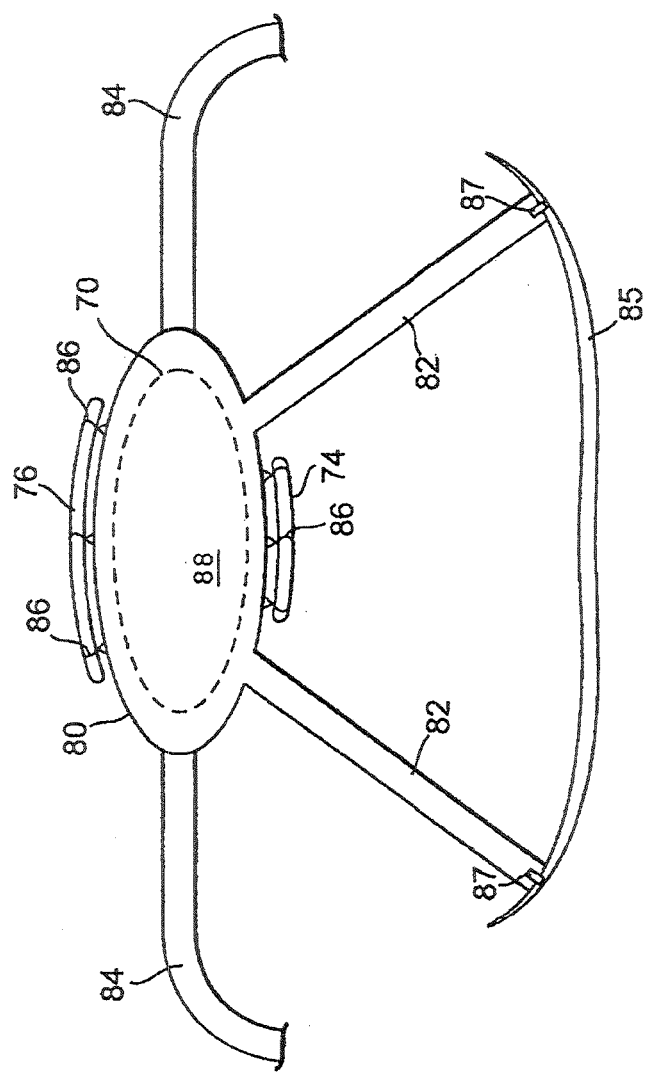
FIG. 8 illustrates relevant pelvic anatomy related to methods as described herein, including an implant.

FIG. 8 illustrates an alternate embodiment of an installed implant of the invention. Vaginal cuff 70 is illustrated in dashed lines, beneath central support portion 80. Central support portion 80 includes two lobe extensions 82, which are each of a length to reach and attach to sacrum 85 with fasteners 87. Extension portions 84, which may be mesh strips, tape, or the like, extend bilaterally from central support portion 80. Central support portion 80 is attached anteriorly to pubocervical fascia 76 and posteriorly to rectovaginal fascia 74, over the pericervical ring (at the vaginal cuff). Sutures 86 are used to attach tissue to central support portion 80. Uterosacral ligaments 72 are removed or not shown. Lobe extensions 82 are of sufficient length to attach to sacrum 85, and may be attached by any useful attachment method and device (87) such as a bone screw, a bone anchor, or adhesive. Extension portions 84 extend through a tissue passage to be placed at or approximately at the level of the pericervical ring.

Figure 9:
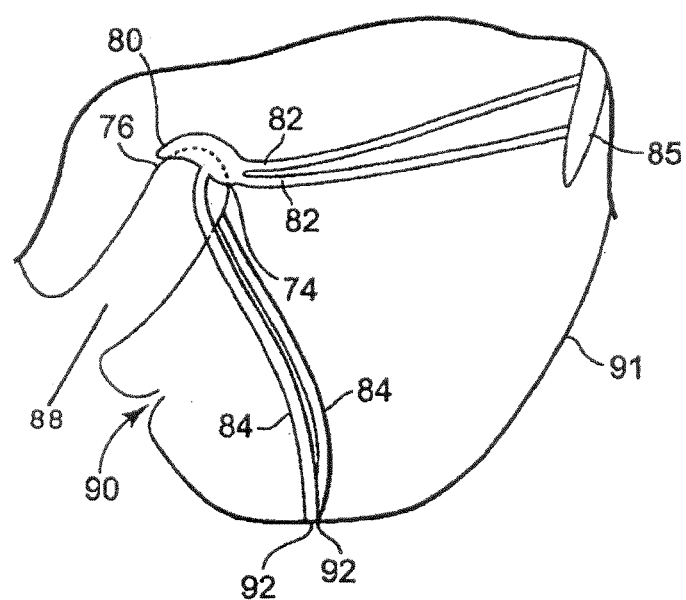
FIG. 9 illustrates relevant pelvic anatomy related to methods as described herein, including an implant.

FIG. 9 illustrates the anatomy following installation of an implant as shown in FIG. 8, from a side three-dimensional view, relative to vagina 88, buttock 91, and rectum 90. As seen in FIG. 9, extension portions 84 extend from central support portion 80 through tissue paths to external incisions 92. In this exemplary embodiment, lobe extensions 82 attach to sacrum 85.

The methods described herein can be used generally to support vaginal tissue, especially to prevent enterocele and vaginal vault prolapse. The implant can be installed either during a hysterectomy procedure to prophylactically prevent enterocele or prolapse, or the implant can be installed later, during a subsequent procedure to a patient who has previously undergone a hysterectomy procedure and developed an enterocele with a vaginal prolapse. The hysterectomy may include full or partial removal of the cervix, or may not remove any tissue of the cervix. The support portion of the implant can be placed on the tissue that remains, which may be the vaginal cuff or the cervix (these tissues being referred to herein for convenience and brevity as the "vaginal cuff").

The surgical installation method can involve methods that are laparoscopic, abdominal (involving an abdominal incision) or a transvaginal. In exemplary transvaginal methods, following attachment of a central support portion of an implant to the vaginal cuff, extension portions of an implant can be secured to support the central support portion and the vaginal cuff. This can be done, e.g., by establishing tissue pathways to exterior incisions and leading the extension portions through the tissue pathways.

Exemplary methods of providing tissue pathways from the vaginal region to external incisions, for installing an implant to support vaginal tissue, are described in U.S. patent application Ser. No. 10/834,943, entitled "Method and Apparatus for Treating Pelvic Organ Prolapse," filed Apr. 30, 2004. Other methods will also be useful. As described in the referenced patent application, two tissue pathways are established between the external perirectal region and the region of the ischial spine. Tools useful for this procedure can be straight or curved needles, optionally including a tip with an adapter that cooperates with a tip or dilator at the end of extension portions of the implant, to allow the dilator of the end portion to be attached to the tip of the needle to lead the dilator and extension portion to a desired location, e.g., through a tissue path to an external incision.

A useful needle can be generally curved or arcuate. A variety of needle designs may be used including, without limitation, straight, bent, curved, arc-shaped, Stamey, Raz and other configurations. Another tool that may be useful is a tunneler (e.g., the IVS Tunneler device available commercially from Tyco), which can also be inserted from an external incision to attach to an end of an extension portion to allow the extension portion to be led from the pelvic region to an external location.

An exemplary pathway can be made by making two external incisions in the rectal area, and a vaginal incision at the vaginal apex. A needle or other instrument can be passed from the external incision to the vaginal region, to contact the extension portion of an implant. Following passage of the needle or instrument through the tissue pathways, the needle or instrument tip can be connected to an extension portion of the implant. Following proper positioning and attachment of the central support portion of the implant to the vaginal cuff, the needle or instrument can be retracted back through the tissue path and through external incision, carrying the extension portion to the external incision.

The invention claimed is:

1. A method of supporting vaginal tissue in a patient with no uterus, the method comprising
 introducing a surgical implant comprising a support portion, an anterior lobe, a posterior lobe, and two posterior lobe extensions,
 extending one of the two posterior lobe extensions between sacral anatomy and vaginal tissue,
 attaching one of the two posterior lobe extensions to sacral anatomy,
 attaching the support portion to the vaginal tissue,
 attaching the anterior lobe to anterior vaginal tissue, and
 attaching the posterior lobe to posterior vaginal tissue,
 whereby the support portion is located in a therapeutic relationship to the vaginal tissue being supported.

2. The method of claim 1, wherein the support portion comprises a non-woven film.

3. The method of claim 1, wherein the two posterior lobe extensions comprise a non-woven film.

4. The method of claim 1, wherein attaching one of the two posterior lobe extensions comprises attaching with a fastener, wherein the fastener comprises a screw.

5. The method of claim 1, wherein the support portion is sutured to an apex of the vaginal tissue.

6. The method of claim 1, wherein the implant is a multi-component implant, and is assembled prior to implantation.

* * * * *